(12) United States Patent
Aqad et al.

(10) Patent No.: US 9,921,475 B1
(45) Date of Patent: Mar. 20, 2018

(54) PHOTOACID-GENERATING COMPOUND, POLYMER DERIVED THEREFROM, PHOTORESIST COMPOSITION INCLUDING THE PHOTOACID-GENERATING COMPOUND OR POLYMER, AND METHOD OF FORMING A PHOTORESIST RELIEF IMAGE

(71) Applicant: Rohm and Haas Electronic Materials LLC, Marlborough, MA (US)

(72) Inventors: Emad Aqad, Northborough, MA (US); William Williams, III, Ipswich, MA (US); Cong Liu, Shrewsbury, MA (US)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 0 days.

(21) Appl. No.: 15/252,522

(22) Filed: Aug. 31, 2016

(51) Int. Cl.
  *G03F 7/004* (2006.01)
  *G03F 7/38* (2006.01)
  *C07C 69/753* (2006.01)
  *C07C 303/32* (2006.01)
  *C07C 309/00* (2006.01)
  *C07C 309/12* (2006.01)
  *C08F 218/14* (2006.01)
  *G03F 7/039* (2006.01)
  (Continued)

(52) U.S. Cl.
  CPC .......... *G03F 7/0045* (2013.01); *C07C 69/753* (2013.01); *C07C 303/32* (2013.01); *C07C 309/00* (2013.01); *C07C 309/12* (2013.01); *C07C 321/30* (2013.01); *C08F 218/14* (2013.01); *C08F 232/08* (2013.01); *G03F 7/039* (2013.01); *G03F 7/2053* (2013.01); *G03F 7/30* (2013.01); *G03F 7/322* (2013.01); *G03F 7/38* (2013.01); *C07C 2102/42* (2013.01); *C07C 2103/74* (2013.01)

(58) Field of Classification Search
  CPC ........ G03F 7/0045; G03F 7/0392; G03F 7/30; G03F 7/38; C07C 69/753; C07C 303/32; C07C 309/00; C07C 309/12; C08F 232/08
  USPC ......... 430/270.1, 921, 922, 207.1, 326, 914; 526/281; 560/120, 128; 562/100, 109, 562/110, 113
  See application file for complete search history.

(56) References Cited

U.S. PATENT DOCUMENTS 2,760,863 A  8/1956 Plambeck, Jr.
2,850,445 A  9/1958 Oster
(Continued)

*Primary Examiner* — John S Chu
(74) *Attorney, Agent, or Firm* — Cantor Colburn LLP

(57) ABSTRACT

A photoacid-generating compound has the structure

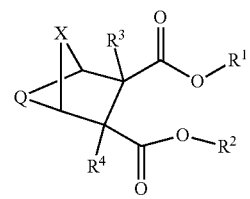

where $R^1$, $R^2$, $R^3$, $R^4$, Q, and X are defined herein. The photoacid-generating compound can be used as a component of a photoresist composition, or as a monomer incorporated into a polymer useful in a photoresist composition. The photoacid-generating compound provides a desired balance of solubility and line width roughness.

11 Claims, 1 Drawing Sheet

(51) Int. Cl.
*G03F 7/20* (2006.01)
*G03F 7/32* (2006.01)
*C07C 321/30* (2006.01)
*G03F 7/30* (2006.01)
*C08F 232/08* (2006.01)

(56) References Cited

U.S. PATENT DOCUMENTS

| | | |
|---|---|---|
| 2,875,047 A | 2/1959 | Oster |
| 3,097,096 A | 7/1963 | Oster |
| 3,427,161 A | 2/1969 | Laridon et al. |
| 3,479,185 A | 11/1969 | Chambers, Jr. |
| 3,549,367 A | 12/1970 | Chang et al. |
| 4,343,885 A | 8/1982 | Reardon, Jr. |
| 6,358,666 B1 * | 3/2002 | Seo ................... C08F 232/08 430/270.1 |
| 8,431,325 B2 | 4/2013 | Hashimoto et al. |
| 8,852,846 B2 * | 10/2014 | Anryu ................ C07D 279/12 430/270.1 |
| 2009/0202943 A1 | 8/2009 | Ohsawa et al. |
| 2011/0200936 A1 | 8/2011 | Ichikawa et al. |
| 2011/0217654 A1 * | 9/2011 | Yamato ............... C07C 271/24 430/270.1 |
| 2011/0287362 A1 | 11/2011 | Seshimo et al. |
| 2013/0209938 A1 * | 8/2013 | Takihana ........... C07C 309/10 430/285.1 |
| 2013/0280658 A1 * | 10/2013 | Maruyama ......... C07C 309/27 430/285.1 |

* cited by examiner

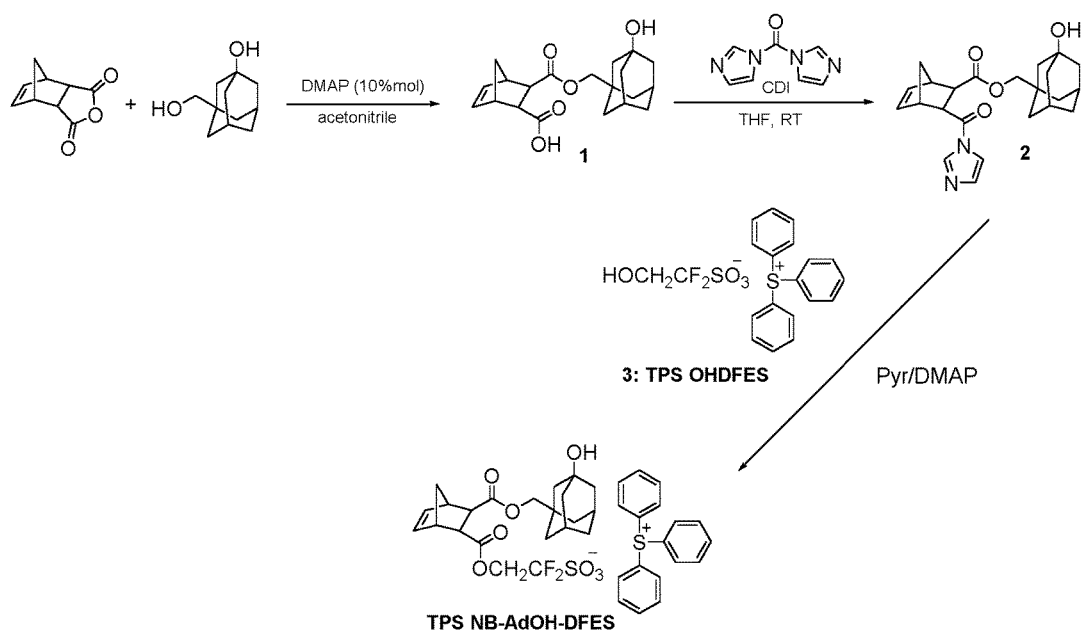

PHOTOACID-GENERATING COMPOUND, POLYMER DERIVED THEREFROM, PHOTORESIST COMPOSITION INCLUDING THE PHOTOACID-GENERATING COMPOUND OR POLYMER, AND METHOD OF FORMING A PHOTORESIST RELIEF IMAGE

FIELD

The present invention relates to a photoacid-generating compound, a polymer formed from an embodiment of the photoacid-generating compound comprising a polymerizable group, a photoresist composition comprising the photoacid-generating compound, the polymer, or a combination thereof, and a method of forming a photoresist relief image with the photoresist composition.

INTRODUCTION

Advance lithographic techniques such as electron beam and Extreme Ultraviolet (EUV) lithographies are being used for the formation of fine patterns. Further shrinking of pattern size to 25 nanometers and less requires, in addition to other process and exposure tool related requirements, the development of highly resolving chemically amplified photoresist compositions. The use of slow diffusion photoacid-generating (PAG) compounds has proved to be critical for the improvement in resolution and pattern quality. Slow acid diffusion in a chemically amplified photoresist composition was achieved by attaching the acidic unit to one or more bulky substituents. However, the use of bulky substituents often decreases the solubility of the PAG compound, which is associated with PAG compound aggregation and/or inhomogeneous PAG compound distribution in the photoresist layer, and with the formation of defects during and after lithographic processing.

There remains a need for photoacid-generating compounds that exhibit an improved balance of solubility and line width roughness, without compromising the short acid diffusion characteristic of low-solubility PAG compounds with bulky substituents.

SUMMARY

One embodiment is a photoacid-generating compound having the structure

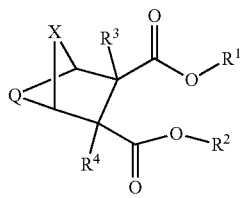

wherein $R^1$ is a $C_{6-20}$ polycyclic hydrocarbyl group comprising a hydroxyl group, a lactone group, or a combination thereof; $R^2$ is a $C_{6-20}$ polycyclic hydrocarbyl group comprising a hydroxyl group, a lactone group, or a combination thereof; or —[(CH$_2$)$_n$—Y—SO$_3^-$Z$^+$], wherein n is 0, 1, or 2; Y is a $C_{1-4}$ alkylene group comprising at least one fluorine atom, provided that when n is 0, Y is a $C_{2-4}$ alkylene group comprising at least one fluorine atom;

and $Z^+$ is an organic cation; $R^3$ and $R^4$ are each independently hydrogen, cyano, $C_{1-6}$ alkyl, $C_{1-6}$ fluoroalkyl, optionally substituted $C_{6-12}$ aryl, or —C(O)O—$R^{11}$ wherein $R^{11}$ is a $C_{1-20}$ alkyl group optionally comprising one or more heteroatoms; and Q is

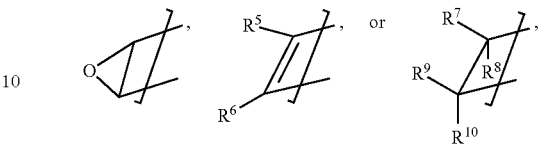

wherein $R^5$ and $R^6$ are each independently hydrogen, fluorine, cyano, trifluoromethyl, $C_{1-6}$ alkyl, $C_{6-20}$ hydrocarbyl comprising a lactone group, or —OR$^{12}$ wherein $R^{12}$ is $C_{1-20}$ alkyl, or $C_{6-20}$ hydrocarbyl comprising a lactone group; and $R^7$, $R^8$, $R^9$, and $R^{10}$ are each independently hydrogen; hydroxyl: —OR$^{13}$ wherein $R^{13}$ is a $C_{1-20}$ hydrocarbyl group optionally comprising one or more heteroatoms; —SR$^{13}$ wherein $R^{13}$ is defined above; —OC(O)R$^{13}$ wherein $R^{13}$ is defined above; —N(R$^{14}$)C(O)R$^{13}$ wherein $R^{13}$ is defined above and $R^{11}$ is hydrogen or a $C_{1-20}$ hydrocarbyl group optionally comprising one or more heteroatoms; —[OC(O)C(R$^a$)=CH$_2$] wherein $R^a$ is hydrogen or fluoro or cyano or $C_{1-10}$ alkyl or $C_{1-10}$ fluoroalkyl; —[O—(CH$_2$)$_n$—Y—SO$_3^-$Z$^+$] wherein n, Y, and $Z^+$ are defined above, —[S—(CH$_2$)$_n$—Y—SO$_3^-$Z$^+$] wherein n, Y, and $Z^+$ are defined above, or —[O—C(O)—(CH$_2$)$_n$—Y—SO$_3^-$Z$^+$] wherein n, Y, and $Z^+$ are defined above; and X is —CH$_2$—, —O—, —C(O)—, —S(O)—, or —S(O)$_2$—; provided that the photoacid-generating compound comprises exactly one occurrence of —[(CH$_2$)$_n$—Y—SO$_3^-$Z$^+$], 1 or 2 occurrences of the $C_{6-20}$ polycyclic hydrocarbyl group comprising a hydroxyl group, a lactone group, or a combination thereof, and 1, 2, or 3 total occurrences of hydroxyl groups and lactone groups; and provided that when Q is

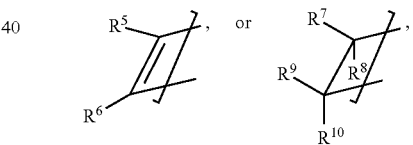

and $R^5$, $R^6$, $R^7$, $R^8$, $R^9$, and $R^{10}$ are hydrogen, and $R^2$ is —[(CH$_2$)$_n$—Y—SO$_3^-$Z$^+$], then $R^1$ excludes —C(O)O— groups and —S(O)$_2$— groups.

Another embodiment is polymer comprising repeat units derived from a polymerizable embodiment of the photoacid-generating compound wherein Q is

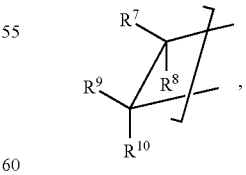

wherein one of $R^7$ and $R^9$ is hydrogen or hydroxyl and the other of $R^7$ and $R^9$ is hydrogen; wherein one of $R^8$ and $R^{10}$ is —[OC(O)C(R$^a$)=CH$_2$] wherein $R^a$ is hydrogen, fluoro, cyano, $C_{1-10}$ alkyl, or $C_{1-10}$ fluoroalkyl, and the other of $R^8$ and $R^{10}$ is hydrogen; and wherein $R^2$ is —[(CH$_2$)$_n$—Y—SO$_3^-$Z$^+$], wherein n is 0, 1, or 2; Y is a $C_{1-4}$ alkylene group comprising at least one fluorine atom, provided that when n is 0, Y is a $C_{2-4}$ alkylene group comprising at least one fluorine atom; and $Z^+$ is an organic cation.

Another embodiment is a photoresist composition comprising the polymer.

Another embodiment is a method of forming a photoresist relief image, comprising: (a) applying a layer of a photoresist composition of claim 9 on a substrate to form a photoresist layer; (b) pattern-wise exposing the photoresist layer to activating radiation to form an exposed photoresist layer; and (c) developing the exposed photoresist layer to provide a photoresist relief image.

These and other embodiments are described in detail below.

BRIEF DESCRIPTION OF THE DRAWING

The FIGURE is a chemical scheme for the synthesis of the photoacid generator compound designated TPS NB-AdOH-DFES.

DETAILED DESCRIPTION

The present inventors have determined that photoresist compositions exhibit an improved balance of solubility and line width roughness when they incorporate a photoacid-generating compound having the structure

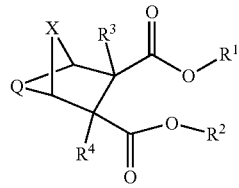

wherein $R^1$ is a $C_{6-20}$ polycyclic hydrocarbyl group comprising a hydroxyl group, a lactone group, or a combination thereof; $R^2$ is a $C_{6-20}$ polycyclic hydrocarbyl group comprising a hydroxyl group, a lactone group, or a combination thereof, or

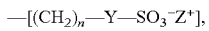

wherein n is 0, 1, or 2; Y is a $C_{1-4}$ alkylene group comprising at least one fluorine atom, provided that when n is 0, Y is a $C_{2-4}$ alkylene group comprising at least one fluorine atom; and $Z^+$ is an organic cation; $R^3$ and $R^4$ are each independently hydrogen, cyano, $C_{1-6}$ alkyl, $C_{1-6}$ fluoroalkyl, optionally substituted $C_{6-12}$ aryl, or —C(O)O—$R^{11}$ wherein $R^{11}$ is a $C_{1-20}$ alkyl group optionally comprising one or more heteroatoms; and Q is

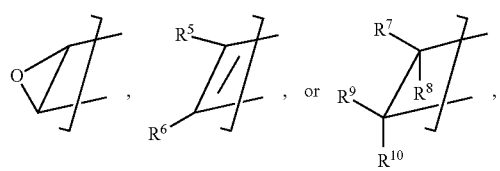

wherein $R^5$ and $R^6$ are each independently hydrogen, fluorine, cyano, trifluoromethyl, $C_{1-6}$ alkyl, $C_{6-20}$ hydrocarbyl comprising a lactone group, or —$OR^{12}$ wherein $R^{12}$ is $C_{1-20}$ alkyl, or $C_{6-20}$ hydrocarbyl comprising a lactone group; and $R^7$, $R^8$, $R^9$, and $R^{10}$ are each independently hydrogen; hydroxyl: —$OR^{13}$ wherein $R^{13}$ is a $C_{1-20}$ hydrocarbyl group optionally comprising one or more heteroatoms; —$SR^{13}$ wherein $R^{13}$ is defined above; —OC(O)$R^{13}$ wherein $R^{13}$ is defined above; —N($R^{14}$)C(O)$R^{13}$ wherein $R^{13}$ is defined above and $R^{11}$ is hydrogen or a $C_{1-20}$ hydrocarbyl group optionally comprising one or more heteroatoms; —[OC(O)C($R^a$)=$CH_2$] wherein $R^a$ is hydrogen or fluoro or cyano or $C_{1-10}$ alkyl or $C_{1-10}$ fluoroalkyl; —[O—$(CH_2)_n$—Y—$SO_3^-Z^+$] wherein n, Y, and $Z^+$ are defined above, —[S—$(CH_2)_n$—Y—$SO_3^-Z^+$] wherein n, Y, and $Z^+$ are defined above, or —[O—C(O)—$(CH_2)_n$—Y—$SO_3^-Z^+$] wherein n, Y, and $Z^+$ are defined above; and X is —$CH_2$—, —O—, —C(O)—, —S(O)—, or —$S(O)_2$—; provided that the photoacid-generating compound comprises exactly one occurrence of —[$(CH_2)_n$—Y—$SO_3^-Z^+$], 1 or 2 occurrences of the $C_{6-20}$ polycyclic hydrocarbyl group comprising a hydroxyl group, a lactone group, or a combination thereof, and 1, 2, or 3 total occurrences of hydroxyl groups and lactone groups; and provided that when Q is

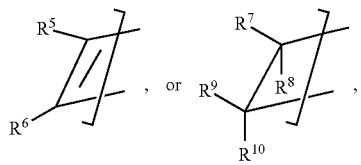

and $R^5$, $R^6$, $R^7$, $R^8$, $R^9$, and $R^{10}$ are hydrogen, and $R^2$ is —[$(CH_2)_n$—Y—$SO_3^-Z^+$], then $R^1$ excludes —C(O)O— groups and —$S(O)_2$— groups.

As used herein, "substituted" means including at least one substituent such as a halogen (i.e., F, Cl, Br, I), hydroxyl, amino, thiol, carboxyl, carboxylate, amide, nitrile, sulfide, disulfide, nitro, $C_{1-18}$ alkyl, $C_{1-18}$ alkoxyl, $C_{6-18}$ aryl, $C_{6-18}$ aryloxyl, $C_{7-18}$ alkylaryl, or $C_{7-18}$ alkylaryloxyl. It will be understood that any group or structure disclosed with respect to the formulas herein may be so substituted unless otherwise specified. "Alkyl" includes linear, branched, cyclic, and polycyclic alkyl, and alkyl groups having a combination of at least two types of linear, branched, cyclic, and polycyclic alkyl fragments. "Fluorinated" means having one or more fluorine atoms incorporated into the group. For example, where a $C_{1-18}$ fluoroalkyl group is indicated, the fluoroalkyl group can include one or more fluorine atoms, for example, a single fluorine atom, two fluorine atoms (e.g., as a 1,1-difluoroethyl group), three fluorine atoms (e.g., as a 2,2,2-trifluoroethyl group), or fluorine atoms at each free valence of carbon (e.g., as a perfluorinated group such as —$CF_3$, —$C_2F_5$, —$C_3F_7$, or —$C_4F_9$). It will be understood that carbon counts for substituted groups include any carbon atoms of substituents. For example, the $C_{1-8}$-alkylene group in "substituted —C(=O)—($C_{1-8}$-alkylene)-C(=O)—" has 1 to 8 carbon atoms, including any carbon atoms derived from substitution.

As used herein, the term "hydrocarbyl", whether used by itself, or as a prefix, suffix, or fragment of another term, refers to a residue that contains only carbon and hydrogen unless otherwise specified. The hydrocarbyl residue can be aliphatic or aromatic, straight-chain, cyclic, bicyclic, polycyclic, or branched, saturated or unsaturated. It can also contain combinations of aliphatic, aromatic, straight chain, cyclic, bicyclic, polycyclic, and branched groups, as well as saturated and unsaturated hydrocarbon moieties. When the hydrocarbyl residue is described as substituted, it can contain heteroatoms in addition to carbon and hydrogen.

One embodiment is a photoacid-generating compound having the structure

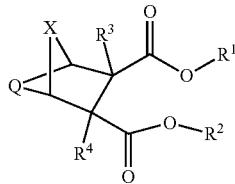

wherein $R^1$, $R^2$, $R^3$, $R^4$, Q, and X are defined herein. No particular stereochemistry is implied or required for the ring carbon atoms bearing the $R^3$ and $R^4$ substituents.

In the photoacid-generating compound structure, $R^1$ is a $C_{6-20}$ polycyclic hydrocarbyl group comprising a hydroxyl group, a lactone group, or a combination thereof. In some embodiments, $R^1$ is

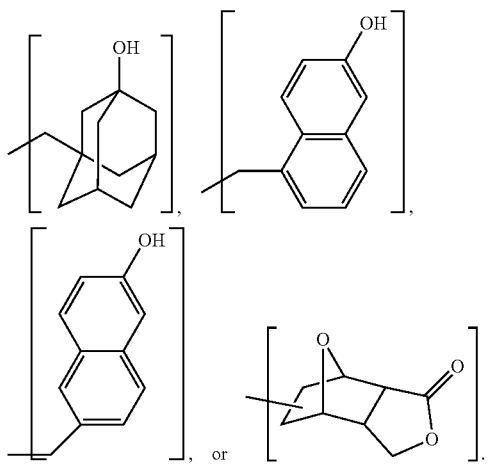

$R^2$ is a $C_{6-20}$ polycyclic hydrocarbyl group comprising a hydroxyl group, a lactone group, or a combination thereof, or

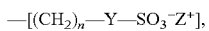

wherein n is 0, 1, or 2; Y is a $C_{1-4}$ alkylene group comprising at least one fluorine atom, provided that when n is 0, Y is a $C_{2-4}$ alkylene group comprising at least one fluorine atom; and $Z^+$ is an organic cation. In some embodiments in which $R^2$ is a $C_{6-20}$ polycyclic hydrocarbyl group comprising a hydroxyl group, a lactone group, or a combination thereof, $R^2$ is

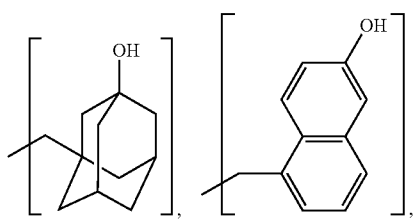

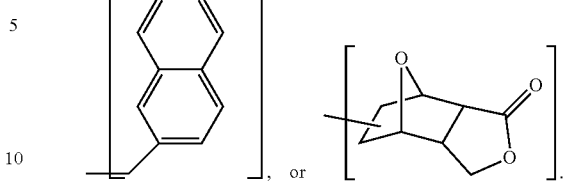

In some embodiments in which $R^2$ is —[($CH_2$)$_n$—Y—$SO_3^-$ $Z^+$], n is 1. In other such embodiments, n is 2. In some embodiments in which $R^2$ is —[($CH_2$)$_n$—Y—$SO_3^-Z^+$], Y is —$CF_2$—. In other such embodiments, Y is —$CF_2CF_2$—.

When $R^2$ is —[($CH_2$)$_n$—Y—$SO_3^-Z^+$], and in any other compound or fragment in which $Z^+$ appears, $Z^+$ is an organic cation. Organic cations include, for example, ammonium ion substituted with 1 to 4 alkyl groups, aryl groups, or a combination of alkyl and aryl groups; iodonium ions substituted with 2 alkyl groups, aryl groups or a combination of alkyl and aryl groups; and sulfonium ion substituted with 3 alkyl groups, aryl groups, or a combination of alkyl or aryl groups. In some embodiments, $Z^+$ is an iodonium or sulfonium cation. In some embodiments, $Z^+$ is an iodonium ion substituted with 2 alkyl groups, aryl groups or a combination of alkyl and aryl groups; or a sulfonium ion substituted with 3 alkyl groups, aryl groups, or a combination of alkyl or aryl groups.

In some embodiments, $Z^+$ has the structure

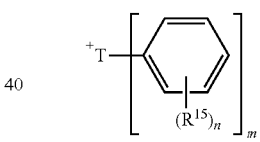

wherein T is I and m is 2, or T is S and m is 3; each $R^{15}$ is independently a halogen, —CN, —OH, a $C_{1-10}$ alkyl group, a $C_{1-10}$ fluoroalkyl group, a $C_{1-10}$ alkoxyl group, a $C_{1-10}$ fluoroalkoxyl group, a $C_{3-10}$ cycloalkyl group, a $C_{3-10}$ fluorocycloalkyl group, a $C_{3-10}$ cycloalkoxyl group, or a $C_{3-10}$ fluorocycloalkoxy group; and each n is an integer of 0, 1, 2, 3, 4, or 5.

In some embodiments, $Z^+$ has the structure

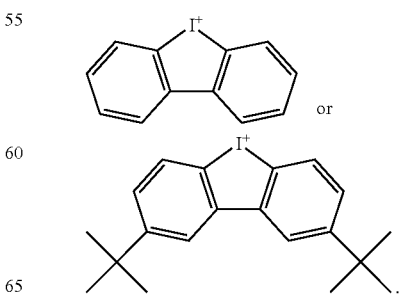

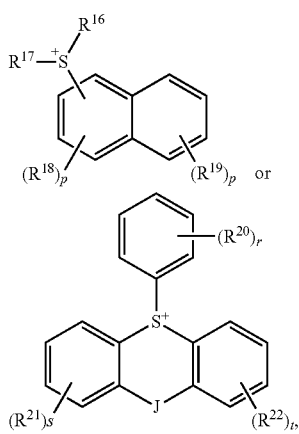

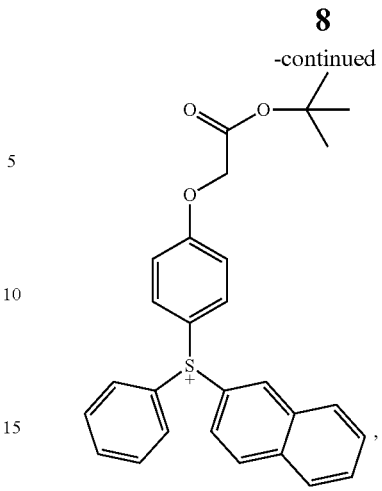

wherein $R^{16}$, $R^{17}$, $R^{18}$, $R^{19}$, $R^{20}$, $R^{21}$, and $R^{22}$ are each independently a halogen, —CN, —OH, a $C_{1-10}$ alkyl group, a $C_{1-10}$ fluoroalkyl group, a $C_{1-10}$ alkoxyl group, a $C_{1-10}$ fluoroalkoxyl group, a $C_{3-10}$ cycloalkyl group, a $C_{3-10}$ fluorocycloalkyl group, a $C_{3-10}$ cycloalkoxyl group, or a $C_{3-10}$ fluorocycloalkoxy group, each of which except a halogen, —CN, and —OH may be substituted or unsubstituted; J is a single bond or a divalent group selected from —S—, —O—, and —C(=O)—; each occurrence of p is independently an integer of 0, 1, 2, 3, or 4; r is 0, 1, 2, 3, 4, or 5; and s and t are each independently 0, 1, 2, 3, or 4. $R^{16}$, $R^{17}$, $R^{18}$, $R^{19}$, $R^{20}$, $R^{21}$, and $R^{22}$ may optionally comprise an acid cleavable group, for example, a $C_{6-10}$ alkoxycarbonylalkyleneoxyl group. An example of a $C_{6-10}$ alkoxycarbonylalkyleneoxyl group is t-butyloxycarbonylmethoxyl group as shown in the following compounds:

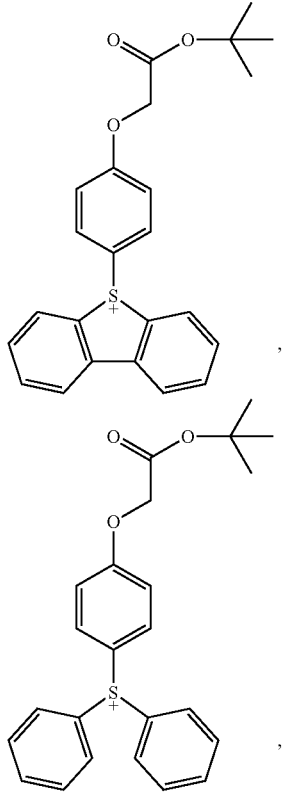

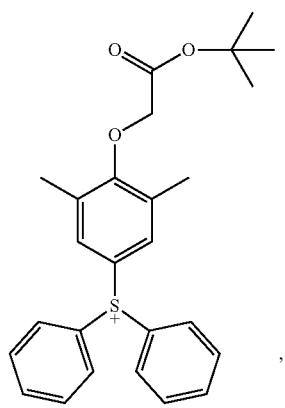

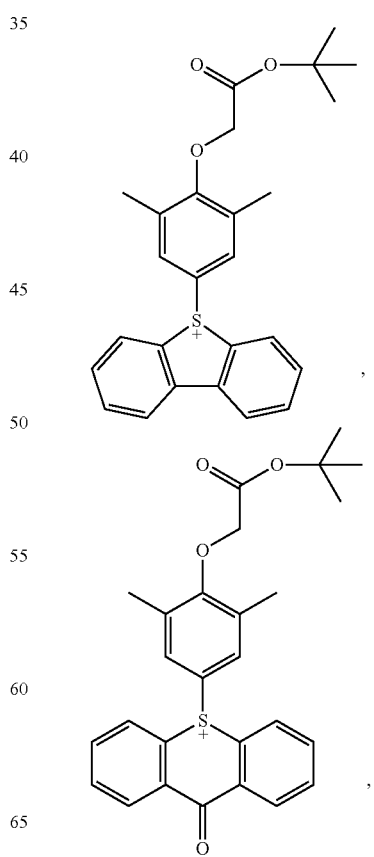

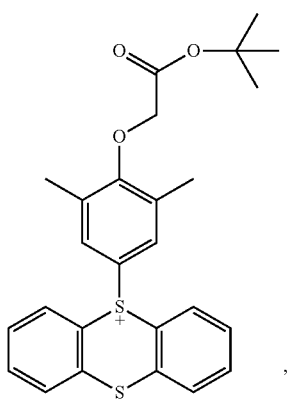
,
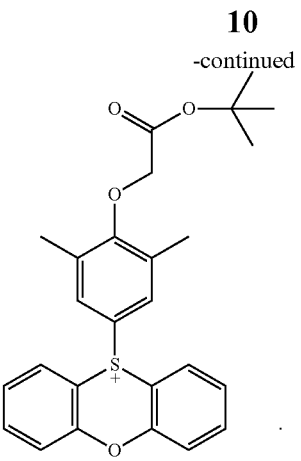
In other embodiments, Z⁺ has the structure
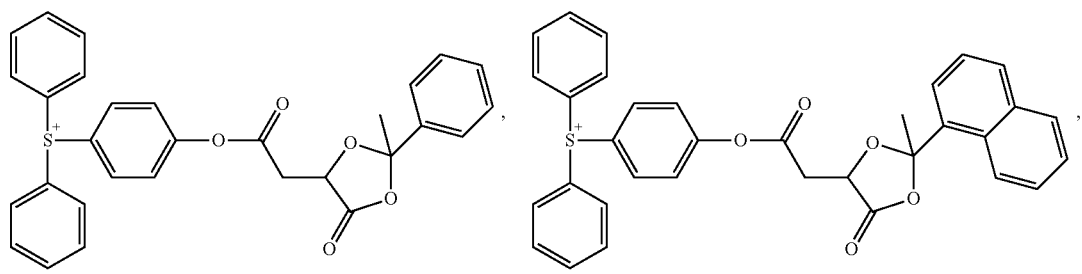
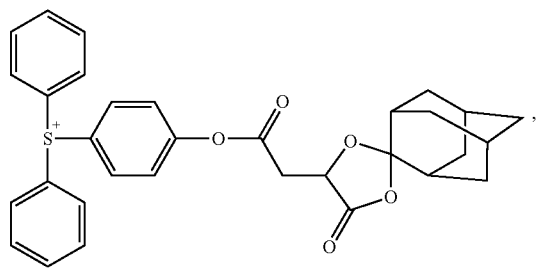
,
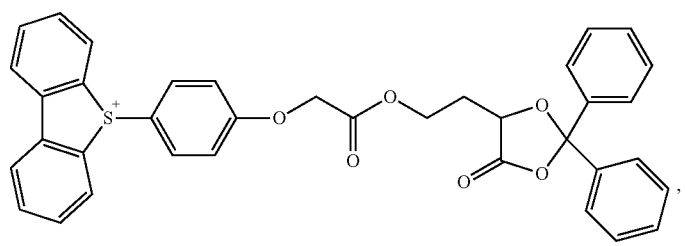
,
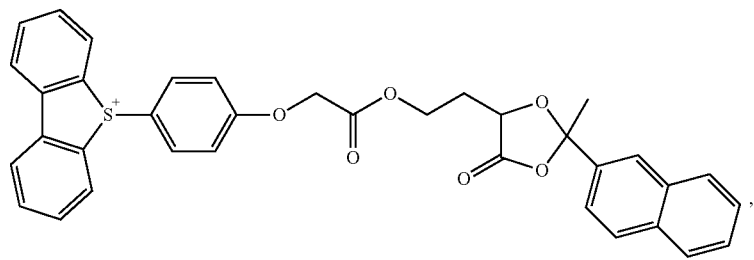
, -continued

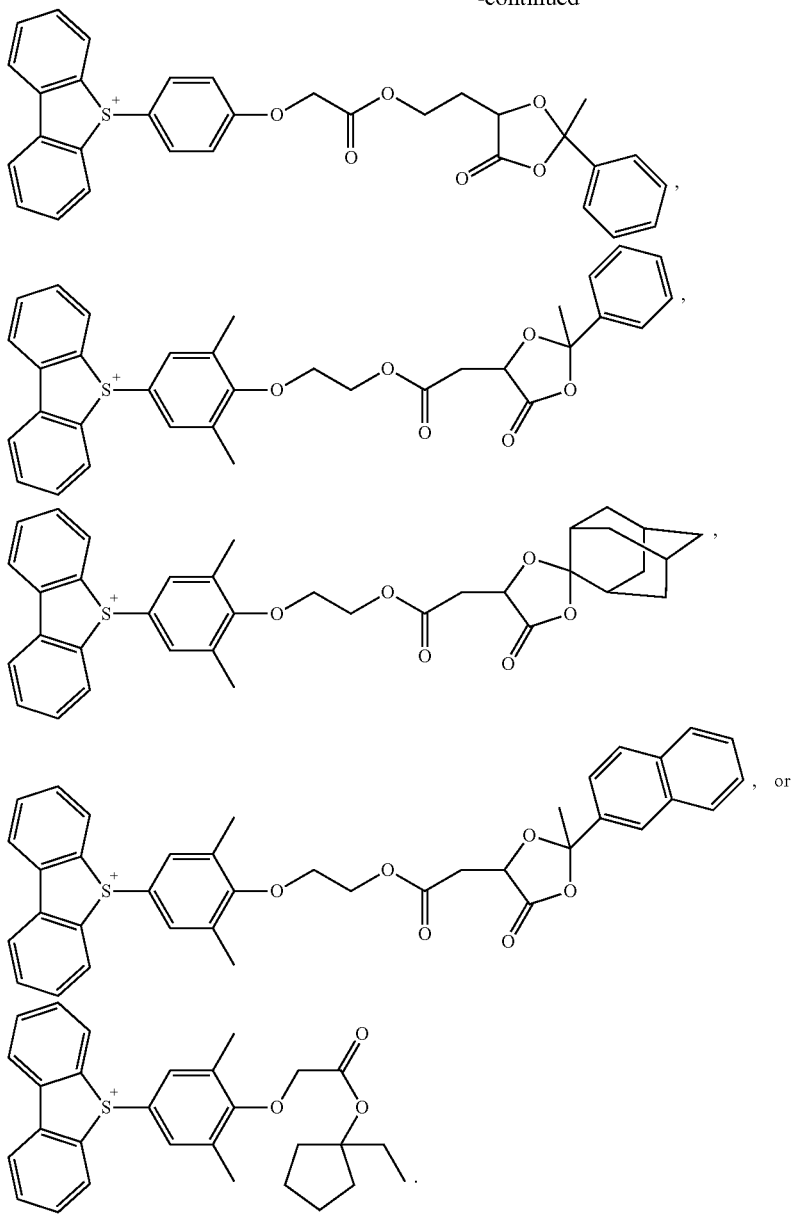

In another embodiment, $Z^+$ has the structure

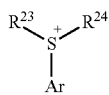

wherein Ar is a $C_{5-30}$ unsubstituted or substituted aromatic group and $R^{23}$ and $R^{24}$ are each independently a $C_{1-10}$ alkyl group, wherein $R^{23}$ and $R^{24}$ are optionally connected together to form a ring. Examples of sulfonium cations in which $R^{23}$ and $R^{24}$ are connected together to form a ring are

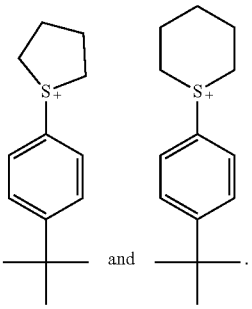

In the photoacid-generating compound structure, $R^3$ and $R^4$ are each independently hydrogen, cyano, $C_{1-6}$ alkyl, $C_{1-6}$ fluoroalkyl, optionally substituted $C_{6-12}$ aryl, or —C(O)O—$R^{11}$ wherein $R^{11}$ is a $C_{1-20}$ alkyl group optionally comprising one or more heteroatoms, each of which can be present in a substituent or replacing a carbon atom in the alkyl group framework. In some embodiments, $R^3$ and $R^4$ are hydrogen.

In the photoacid-generating compound structure, Q is

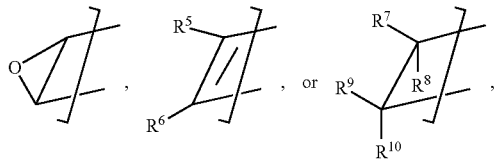

wherein $R^5$ and $R^6$ are each independently hydrogen; fluorine; cyano; trifluoromethyl; $C_{1-6}$ alkyl; $C_{6-20}$ hydrocarbyl comprising a lactone group; or —$OR^{12}$ wherein $R^{12}$ is $C_{1-20}$ alkyl (including $C_{1-6}$ alkyl and $C_{6-20}$ polycyclic alkyl) or $C_{6-20}$ hydrocarbyl comprising a lactone group. $R^7$, $R^8$, $R^9$, and $R^{10}$ are each independently hydrogen; hydroxyl; —$OR^{13}$ wherein $R^{13}$ is a $C_{1-20}$ hydrocarbyl group optionally comprising one or more heteroatoms; —$SR^{13}$ wherein $R^{13}$ is defined above; —$OC(O)R^{13}$ wherein $R^{13}$ is defined above; —$N(R^{14})C(O)R^{13}$ wherein $R^{13}$ is defined above and $R^{14}$ is hydrogen or a $C_{1-20}$ hydrocarbyl group optionally comprising one or more heteroatoms; —[OC(O)C($R^a$)=CH$_2$] wherein $R^a$ is hydrogen or fluoro or cyano or $C_{1-10}$ alkyl or $C_{1-10}$ fluoroalkyl; —[O—(CH$_2$)$_n$—Y—SO$_3^-$Z$^+$] wherein n, Y, and Z$^+$ are defined above, —[S—(CH$_2$)$_n$—Y—SO$_3^-$Z$^+$] wherein n, Y, and Z$^+$ are defined above, or —[O—C(O)—(CH$_2$)$_n$—Y—SO$_3^-$Z$^+$] wherein n, Y, and Z$^+$ are defined above. In some embodiments in which $R^{13}$ comprises a heteroatom, it comprises a lactone group. In some embodiments in which $R^{13}$ comprises a heteroatom, it does not comprise a hydroxyl group.

In the photoacid-generating compound structure, X is —CH$_2$—, —O—, —C(O)—, —S(O)—, or —S(O)$_2$—. In some embodiments, X is —CH$_2$—.

There are certain limitations on the structure of the photoacid-generating compound. First, the photoacid-generating compound comprises exactly one occurrence of —[(CH$_2$)$_n$—Y—SO$_3^-$Z$^+$]. This includes occurrences in which the —[(CH$_2$)$_n$—Y—SO$_3^-$Z$^+$] group is linked to the polycyclic nucleus via —O— or —S— or —OC(O)—. Second, the photoacid-generating compound comprises 1 or 2 occurrences of the $C_{6-20}$ polycyclic hydrocarbyl group comprising a hydroxyl group, a lactone group, or a combination thereof. Third, the photoacid-generating compound comprises 1, 2, or 3 total occurrences of hydroxyl groups and lactone groups, which any hydroxyl or lactone group in the molecule. Fourth, when Q is

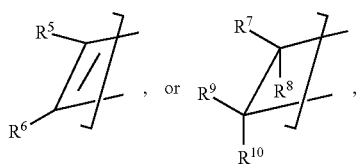

and $R^5$, $R^6$, $R^7$, $R^8$, $R^9$, and $R^{10}$ are hydrogen, and $R^2$ is —[(CH$_2$)$_n$—Y—SO$_3^-$Z$^+$], then $R^1$ excludes —C(O)O— groups and —S(O)$_2$— groups.

In a specific embodiment of the photoacid-generating compound, Q is

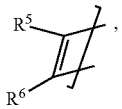

wherein $R^5$ and $R^6$ are hydrogen; and $R^2$ is

—[(CH$_2$)$_n$—Y—SO$_3^-$Z$^+$], wherein n is 0, 1, or 2; Y is a $C_{1-4}$ alkylene group comprising at least one fluorine atom, provided that when n is 0, Y is a $C_{2-4}$ alkylene group comprising at least one fluorine atom; and Z$^+$ is an organic cation.

In another specific embodiment of the photoacid-generating compound, Q is

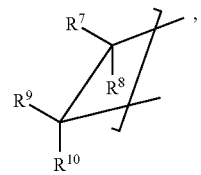

wherein one of $R^7$ and $R^8$ is hydroxyl and the other of $R^7$ and $R^8$ is hydrogen; one of $R^9$ and $R^{10}$ is —[O—(CH$_2$)$_n$—Y—SO$_3^-$Z$^+$], —[OC(O)—(CH$_2$)$_n$—Y—SO$_3^-$Z$^+$], or —[S—(CH$_2$)$_n$—Y—SO$_3^-$Z$^+$], and the other of $R^9$ and $R^{10}$ is hydrogen; and $R^2$ is a $C_{8-12}$ polycyclic hydrocarbyl group comprising a hydroxyl group, a lactone group, or a combination thereof.

In another specific embodiment of the photoacid-generating compound, Q is

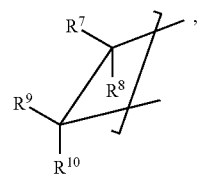

wherein $R^7$ and $R^9$ are hydrogen; wherein one of $R^8$ and $R^{10}$ is —[O—(CH$_2$)$_n$—Y—SO$_3^-$Z$^+$] or —[S—(CH$_2$)$_n$—Y—SO$_3^-$Z$^+$] or —[O—C(O)—(CH$_2$)$_n$—Y—SO$_3^-$Z$^+$] wherein n is 0, 1, or 2, Y is a $C_{1-4}$ alkylene group comprising at least one fluorine atom, and Z$^+$ is an organic cation, and the other of $R^8$ and $R^{10}$ is hydrogen; and $R^2$ is a $C_{8-12}$ polycyclic hydrocarbyl group comprising a hydroxyl group, a lactone group, or a combination thereof.

In another specific embodiment of the photoacid-generating compound, Q is

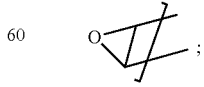

and
$R^2$ is

—[(CH$_2$)$_n$—Y—SO$_3^-$Z$^+$], wherein n is 0, 1, or 2; Y is a $C_{1-4}$ alkylene group comprising at least one fluorine atom, provided that when n is 0, Y is a $C_{2-4}$ alkylene group comprising at least one fluorine atom; and $Z^+$ is an organic cation.

In some embodiments, the photoacid-generating compound is selected from the group consisting of

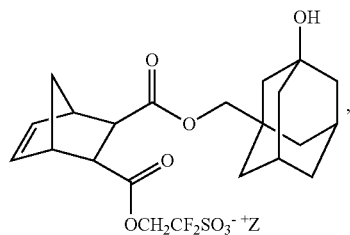

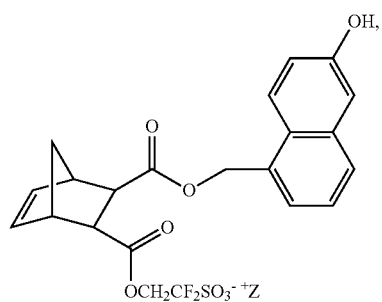

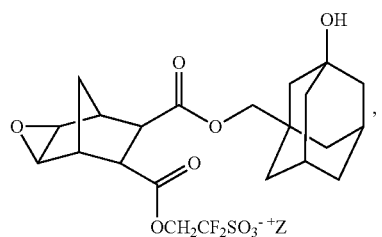

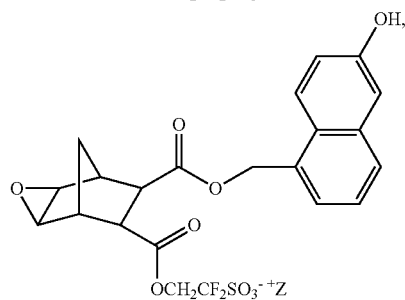

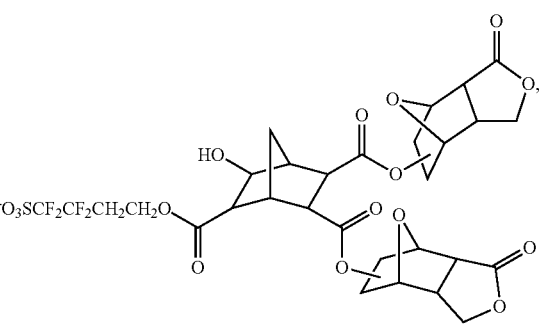

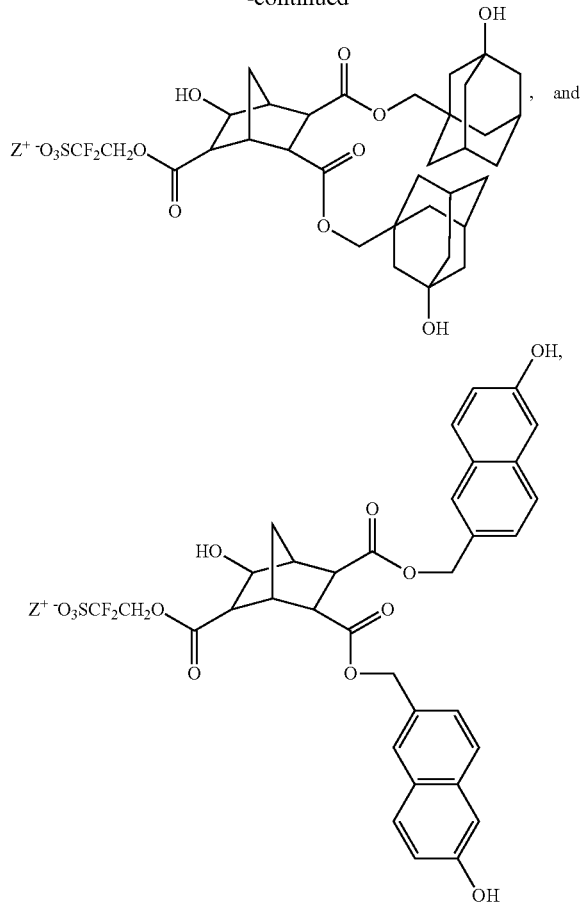

wherein $Z^+$ is an organic cation.

In some embodiments, the photoacid-generating compound comprises a polymerizable group and can be used as a monomer to form photoresist copolymers. For example, in some embodiments, Q is

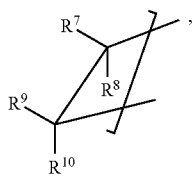

wherein one of $R^7$ and $R^9$ is hydrogen or hydroxyl and the other of $R^7$ and $R^9$ is hydrogen; wherein one of $R^8$ and $R^{10}$ is —[OC(O)C($R^a$)=CH$_2$] wherein $R^a$ is hydrogen, fluoro, cyano, $C_{1-10}$ alkyl, or $C_{1-10}$ fluoroalkyl, and the other of $R^8$ and $R^{10}$ is hydrogen; and wherein $R^2$ is

—[(CH$_2$)$_n$—Y—SO$_3^-$Z$^+$], wherein n is 0, 1, or 2; Y is a $C_{1-4}$ alkylene group comprising at least one fluorine atom, provided that when n is 0, Y is a $C_{2-4}$ alkylene group comprising at least one fluorine atom; and $Z^+$ is an organic cation.

Another embodiment is a polymer comprising repeat units derived from the photoacid-generating compound comprising a polymerizable group, such as, for example, the photoacid-generating compound of the previous paragraph. In addition to repeat units derived from the photoacid-generating compound comprising a polymerizable group, the polymer can, optionally, further comprise one or more of acid-labile monomers (including monomer comprising tertiary ester groups, acetal groups, or ketal groups), base-labile monomers (including monomers comprising lactone groups), and base-ionizable monomers (including monomers comprising 1,1,1,3,3,3-hexafluoro-2-hydroxy-2-propyl groups, —$NHSO_2CH_3$ groups, and —$NHSO_2CF_3$ groups).

Another embodiment is a photoresist composition comprising the polymer of the previous paragraph.

Another embodiment is a photoresist composition comprising the photoacid-generating compound, in any of its above-described variations.

In addition to the photoacid-generating compound or a polymer comprising the residue of the polymerizable photoacid-generating compound, the photoresist composition can further comprise one or more additional components, such as photoinitiators, surfactants, quenchers, solvents, and combinations thereof.

Photoinitiators are used in the photoresist composition for initiating polymerization of the cross-linking agents by generation of free-radicals. Suitable free radical photoinitiators include, for example, azo compounds, sulfur containing compounds, metallic salts and complexes, oximes, amines, polynuclear compounds, organic carbonyl compounds and mixtures thereof as described in U.S. Pat. No. 4,343,885, column 13, line 26 to column 17, line 18; and 9,10-anthraquinone; 1-chloroanthraquinone; 2-chloroanthraquinone; 2-methylanthraquinone; 2-ethylanthraquinone; 2-tert-butylanthraquinone; octamethylanthraquinone; 1,4-naphthoquinone; 9,10-phenanthrenequinone; 1,2-benzanthraquinone; 2,3-benzanthraquinone; 2-methyl-1,4-naphthoquinone; 2,3-dichloronaphthoquinone; 1,4-dimethylanthraquinone; 2,3-dimethylanthraquinone; 2-phenylanthraquinone; 2,3-diphenylanthraquinone; 3-chloro-2-methylanthraquinone; retenequinone; 7,8,9,10-tetrahydronaphthalenequinone; and 1,2,3,4-tetrahydrobenz(a)anthracene-7,12-dione. Other photoinitiators are described in U.S. Pat. No. 2,760,863 and include vicinal ketaldonyl alcohols, such as benzoin, pivaloin, acyloin ethers, e.g., benzoin methyl and ethyl ethers; and alpha-hydrocarbon-substituted aromatic acyloins, including alpha-methylbenzoin, alpha-allylbenzoin, and alpha-phenylbenzoin. Photoreducible dyes and reducing agents disclosed in U.S. Pat. Nos. 2,850,445; 2,875,047; and 3,097,096 as well as dyes of the phenazine, oxazine, and quinone classes; benzophenone, 2,4,5-triphenylimidazolyl dimers with hydrogen donors, and mixtures thereof as described in U.S. Pat. Nos. 3,427,161; 3,479,185; and 3,549,367 can be also used as photoinitiators.

Illustrative surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX™ PF-636, PF-6320, PF-656, and PF-6520 fluorosurfactants from Omnova.

Suitable quenchers include, for example, those based on hydroxides, carboxylates, amines, imines and amides. Such quenchers include $C_{1-30}$ organic amines, imines or amides, $C_{1-30}$ quaternary ammonium salts of strong bases (e.g., a hydroxide or alkoxide) or a weak base (e.g., a carboxylate). In some embodiments, the photoresist composition further comprises a quencher selected from the group consisting of $C_{1-30}$ amines, $C_{1-30}$ amides, and combinations thereof. Exemplary quenchers include amines such as Troger's base; hindered amines such as diazabicycloundecene (DBU), diazabicyclononene (DBN), and tetrahydroxy isopropyl diamine and tert-butyl-4-hydroxy-1-piperidiene carboxylate; ionic quenchers including quaternary alkyl ammonium salts such as tetrabutylammonium hydroxide (TBAH), tetramethylammonium 2-hydroxybenzoic acid (TMA OHBA), and tetrabutylammonium lactate. Suitable quenchers are further described in U.S. Pat. No. 8,431,325 to Hashimoto et al.

The photoresist composition components are typically dissolved in a solvent for dispensing and coating. Exemplary solvents include anisole; alcohols including 1-methoxy-2-propanol, and 1-ethoxy-2-propanol; esters including n-butyl acetate, ethyl lactate, 1-methoxy-2-propyl acetate, methoxyethoxy propionate, and ethoxyethoxy propionate; ketones including cyclohexanone and 2-heptanone; and combinations thereof. The solvent amount can be, for example, 70 to 99 weight percent, specifically 85 to 98 weight percent, based on the total weight of the photoresist composition.

The invention further includes a method of forming a photoresist relief image, comprising: (a) applying a layer of the photoresist composition on a substrate to form a photoresist layer; (b) pattern-wise exposing the photoresist layer to activating radiation to form an exposed photoresist layer; and (c) developing the exposed photoresist layer to provide a photoresist relief image. The method can, optionally, further include (d) etching the resist relief pattern into the underlying substrate. In this embodiment, the photoresist composition can be the photoresist composition incorporating the photoacid-generating compound, or incorporating a polymer comprising a repeat unit derived from a polymerizable embodiment of the photoacid-generating compound. In some embodiments, the pattern-wise exposing comprises exposing with radiation at 193 or 248 nanometers. In other embodiments, the pattern-wise exposing comprises exposing with electron beam or extreme ultraviolet radiation.

All ranges disclosed herein are inclusive of the endpoints, and the endpoints are independently combinable with each other. Each range disclosed herein constitutes a disclosure of any point or sub-range lying within the disclosed range.

The invention is further illustrated by the following non-limiting examples.

Example 1—Synthesis of Photoacid Generator Compound TPS NB-AdOH-DFES

FIG. 1 presents a chemical scheme for the synthesis of the photoacid generator compound referred to as TPS NB-AdOH-DFES. The synthesis process was as follows. To a suspension of 5-norbornene-2,3-dicarboxylicanhydride (20 grams, 122 millimoles) and 3-(hydroxymethyDadamantan-1-ol (22.2 grams, 121.8 millimoles) in acetonitrile (150 milliliters) was added N,N-dimethylaminopyridine (1.5 grams, 12.27 millimoles) and the reaction mixture was stirred at 65° C. for 18 hours. The mixture was cooled to room temperature and concentrated aqueous hydrochloric acid was added until the pH was reduced to 2. The crude product was filtered and dried, before being suspended in ethyl acetate (150 milliliters) and stirred for 30 minutes at room temperature. Filtration produced 28 grams (yield: 66%) of pure product (1) as a white solid. $^1$H NMR (acetone-d6) δ: 6.22 (m, 1H), 6.17 (m 1H), 3.69 (d, 2H), 3.53 (d, 2H), 3.40 (m, 2H), 3.14 (m, 2H), 2.17 (s, 2H), 1.41-1.67 (m, 15H).

Compound 1 (20 grams, 57.7 millimoles) was dissolved in 100 milliliters pyridine, and 1,1'-carbonyldiimidazole (CDI, 9.36 grams, 57.7 millimoles) was added to the solution. The mixture was stirred at room temperature for 2 hours and then warmed to 90° C. Then, 25.0 grams of salt 3 (triphenylsulfonium 1,1-difluoro-2-hydroxyethanesulfonate or TPS OHDFES, synthesized according to reported procedure in U.S. Patent Application Publication No. US 2009/0202943 A1) and 4-dimethylaminopyridine (DMAP, 7.0 grams, 57.3 millimoles) were added, and the mixture was stirred at 100° C. for 24 hours. The reaction mixture was cooled to room temperature and poured into 3 Normal aqueous hydrochloric acid (200 milliliters) and crushed ice (200 grams), and the resulting sticky solid was isolated by decanting the liquids. The sticky residue was dissolved in dichloromethane (100 milliliters) and the solution was washed twice with 100 milliliters 0.1 Normal aqueous hydrochloric acid, once with 100 milliliters 0.1 Normal aqueous sodium hydroxide, and then five times with deionized water. The organic phase was concentrated under reduced pressure and the concentrated solution was poured slowly into methyl-t-butyl ether (20 volumes) to produce the product as white solid. The product was dried under vacuum. Yield: 19.0 g (44%). $^1$H NMR (acetone-d6 δ): 7.98-7.88 (m, 15H), 6.33 (m, 1H), 6.11 (m, 1H), 3.70 (s, 2H), 3.32-3.45 (m, 4H), 2.91 (m, 2H), 2.18 (s, 2H), 1.41-1.67 (m, 15H). $^{19}$F NMR (acetone-d6) δ: −115.71 (s, 2F).

Example 2—Acid Diffusion Length Evaluation

Acid diffusion length was determined as follows. An acid detector layer formulation was prepared by combining Polymer A1 (2-adamantyl-2-propyl methacrylate/alpha-(gamma-butyrolactone) methacrylate/1-hydroxyadamantyl-3-methacrylate terpolymer, 30/50/20 molar ratio, Mw=10,000 grams/mole) shown below (5.981 weight percent of total formulation), and tert-butyl-4-hydroxypiperdine-1-carboxylate as a quencher (0.019 weight percent of total formulation) in a 50/50 (w/w) mixture of propylene glycol methyl ether acetate (PGMEA) and methyl 2-hydroxyisobutyrate (HBM).

Polymer A1

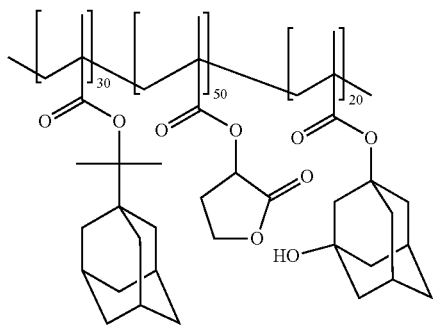

Separately, an acid source layer formulation was prepared by combining a tert-butyl acrylate/methacrylic acid copolymer (70/30 molar ratio, respectively; 0.891% w/w solution) and photoacid generator compound PAG (inventive or comparative) (153.40 micromoles/gram based on the total formulation) in an 80/20 (weight/weight) mixture of 2-methyl-1-butanol and decane. The acid detector layer formulation and acid source layer solutions were each filtered separately using a 0.2 micrometer polytetrafluoroethylene (PTFE) syringe filter.

The substrate (Si wafer, 200 millimeter diameter) was coated with AR™77 antireflective coating (Rohm and Haas Electronic Materials, Marlborough, Mass.) and baked at 205° C. for 60 seconds to form an antireflective layer of 84 nanometer thickness. A 120 nanometer thickness of the acid detector layer formulation was coated on the antireflective layer and baked at 110° C. for 60 seconds. The acid source layer formulation was then coated on the acid detector layer and baked at 90° C. for 60 seconds. All coating processes were carried out on a TEL ACT 8 coating track manufactured by Tokyo Electron.

The coated wafer was then open-frame exposed over 100 dose increments (separate doses) starting from an initial dose of 1 millijoule/centimeter$^2$ (mJ/cm$^2$) at increments of 0.2 mJ/cm$^2$ using a 193 nanometer exposure tool (ASML 1100 Stepper) and annular illumination. The wafer was post-exposure baked (PEB) at 100° C. for 60 seconds or 110° C. for 60 seconds. During the PEB step the acid released during exposure in the acid source layer diffused into the acid detector layer causing deprotection of the acid labile group of the polymer of the acid detector layer. After PEB, the pattern was developed using 0.26 Normal aqueous tetramethylammonium hydroxide (TMAH) solution. The film thickness difference between the unexposed regions and exposed regions of the pattern is the total film thickness loss (ΔL). The greater the film thickness loss in the exposed region, the greater the acid diffusion.

The diffusivity of the PAG, D, is defined by Fick's law of diffusion (equation 1):

$$D=(\Delta L/2 * erfc\ E_{th}/E)^2/t_{PEB} \qquad \text{(equation 1)}$$

where ΔL is the difference in thickness between the exposed and unexposed areas (also referred to herein as the film thickness loss), $t_{PEB}$ is the PEB time, erfc is the error function complement, $E_{th}$ is the exposure dose (in mJ/cm$^2$) at which film thickness loss was observed for the first time, and E is the exposure dose (in mJ/cm$^2$). Once the diffusivity was determined, the diffusion length, DL, was then calculated using equation 2:

$$DL=2*(D*t_{PEB})^{1/2} \qquad \text{(equation 2)}$$

The diffusion length data for PAG in accordance with the invention and comparative PAGs are summarized below in Table 1. Chemical structures of the comparative PAGs are shown below the table.

TABLE 1

|  | Comparative PAG 1 | Comparative PAG 2 | Comparative PAG 3 | TPS NB-AdOH-DFES |
|---|---|---|---|---|
| DL (nm) at PEB 100° C. | 10.9 | 8.1 | 5.1 | 2.6 |
| DL (nm) at PEB 110° C. | 37.4 | 21.9 | 19.4 | 18.2 |

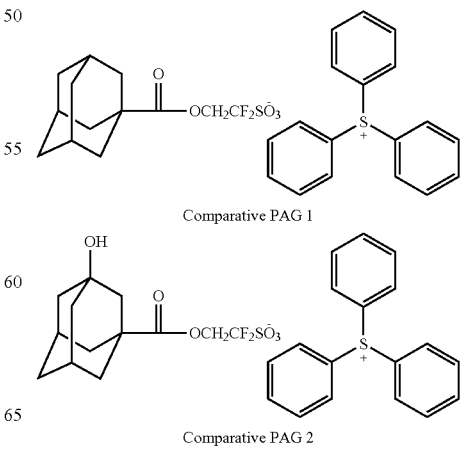

Comparative PAG 1

Comparative PAG 2

TABLE 1-continued

| | Comparative PAG 1 | Comparative PAG 2 | Comparative PAG 3 | TPS NB-AdOH-DFES |
|---|---|---|---|---|

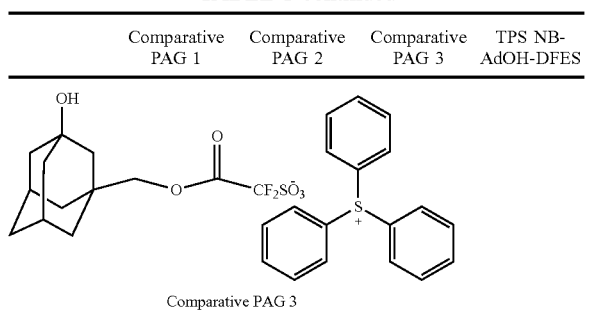

Comparative PAG 3

As can be seen in Table 1, the acid diffusion measurements indicate shorter acid diffusion length for acid generated from PAG according to the invention in comparison with the comparative PAGs.

Example 3—Lithographic Evaluation

Lithographic evaluation of the exemplary PAG was carried out according to the following procedure. Photoresists were formulated using the components and proportions shown in Table 2. The photoresist polymer ("Polymer A2") used in all examples was a pentapolymer incorporating monomers M1, M2, M3, M4 and M5 having the chemical structures shown below, where the mole percentage of M1/M2/M3/M4/M5 is 20/20/30/20/10 for a total of 100 mole percent of monomers. The weight average molecular weight of the polymer was 8,000 grams/mole.

M1

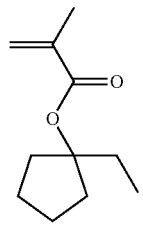

M2

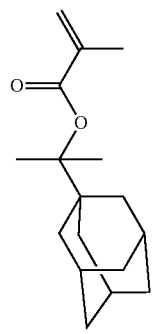

M3

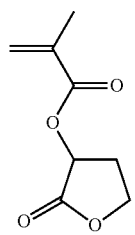

M4

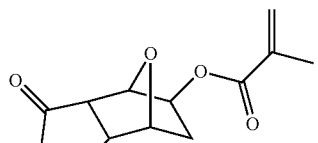

M5

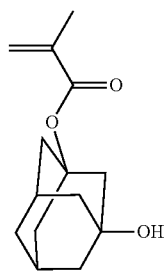

The PAG (see Table 2), base (t-butyloxycarbonyl-4-hydroxypyridine (TBOC-4HP), and surface leveling agent (PF 656 surfactant, available from Omnova), are given as weight percent based on 100% solids content, with the balance of the solids being the polymer. Propylene glycol monomethyl ether acetate (51) and methyl-2-hydroxyisobutyrate (55) were used as the solvents. The weight ratio of solvent S1:S5 in the final formulation was 1:1. The final percent solids in each of the Comparative Examples 1 and 2, and in the Example, was 4 weight percent (wt %).

Photoresist formulation compositions for Comparative Examples A1 and A2 and Example B are shown in Table 2 below.

TABLE 2

| | PAG | PAG wt % | Base wt % | SLA wt % |
|---|---|---|---|---|
| C. Ex. A1 | Triphenylsulfonium perfluorobutane-sulfonate | 9.59 | 1.03 | 0.1 |
| C. Ex. A2 | Comparative PAG 3 | 10.27 | 1.03 | 0.1 |
| Ex. B | TPS NB-AdOH-DFES | 12.83 | 1.03 | 0.1 |

The Table 2 photoresists were lithographically processed as follows. The photoresist was spin coated onto a 200 millimeter diameter silicon wafer having an 84 nanometer thickness of an organic antireflective coating (AR™77, Dow Electronic Materials) and baked at 110° C. for 60 seconds, to form a resist film 100 nanometers in thickness. The photoresist was exposed with ArF excimer laser (193 nanometers) through a mask pattern targeting a line and space pattern (L/S pattern) having a line width of 90 nanometers and a pitch of 180 nanometers, using an ArF exposure apparatus ASML-1100 (manufactured by ASML), NA (numerical aperture)=0.75 under annular illumination with outer/inner sigma of 0.89/0.64 with focus offset/step of 0.10/0.05. The wafers were post exposure baked (PEB) at 100° C. for 60 seconds followed by developing with 0.26 Normal aqueous tetramethylammonium hydroxide (TMAH) developer and subsequent water wash.

In each example, a line/space pattern having a line width of 90 nanometers and a pitch of 180 nanometers was formed. Line Width Roughness (LWR) was determined by processing the image captured by top-down scanning electron microscopy (SEM) using a Hitachi 9380 CD-SEM, operating at an accelerating voltage of 800 volts (V), probe current of 8.0 picoamperes (pA), and 200 K× magnification. The Clearing Dose, $E_0$ (mJ/cm$^2$), is the amount of exposure energy required to clear the resist. $E_0$ is determined from the resist contrast curve, which is a plot of the film thickness of resist remaining after exposure and development as a function of exposure energy. The exposure at which the film clears completely is the clearing dose. The Dose-To-Size, $E_{size}$ (mJ/cm$^2$), is the amount of the exposure energy required to produce a line/space pattern having a line width of 90 nanometers and a pitch of 180 nanometers.

The results from the lithographic evaluation of the above photoresist formulations are shown in Table 3.

TABLE 3

|  | C. Ex. A1 | C. Ex. A2 | Ex. B |
| --- | --- | --- | --- |
| $E_0$ (mJ/cm$^2$) | 5.2 | 9.6 | 10.2 |
| $E_{size}$ (mJ/cm$^2$) | 22.5 | 44.8 | 48.1 |
| LWR 3σ (nm) | 12.8 | 12.4 | 12.0 |

As seen in Table 3, inventive Example B, which includes the PAG designated TPS NB-AdOH-DFES, showed improved (reduced) Line Width Roughness relative to the comparative examples.

Example 4—Solubility Test

The photoacid generators were evaluated for solubility in a selection of organic solvents useful as formulation solvents or as negative tone photoresist developers. Solubility of each of the compounds was obtained for attempts to completely dissolve the compound at 2 weight percent at room temperature (23° C.). The results for the solubility tests are shown in Table 4. Clearly, the PAG from the invention TPS NB-AdOH-DFES has better solubility in formulation solvents such as propyleneglycol monomethyl ether acetate and propyleneglycol monomethyl ether, as well as in solvents that can be used as negative tone organic developers, such as 2-hepanone and n-butyl acetate.

TABLE 4

| | PAG | |
| --- | --- | --- |
| Solvent | Comparative PAG 3 | TPS NB-AdOH-DFES |
| Propyleneglycol monomethyl ether acetate | X | ○ |
| Ethyl lactate | ○ | ○ |
| Propyleneglycol monomethyl ether | X | ○ |
| Methyl-2-hydroxyisobutyrate | ○ | ○ |
| 2-heptanone | X | ○ |
| n-butyl acetate | X | ○ |

○: compound soluble at 2 wt %
X: compound is insoluble at 1%

The invention claimed is:
1. A photoacid-generating compound having the structure

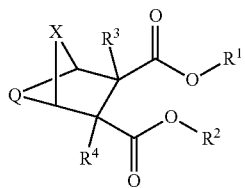

wherein
$R^1$ is a $C_{6-20}$ polycyclic hydrocarbyl group comprising a hydroxyl group, a lactone group, or a combination thereof;
$R^2$ is a $C_{6-20}$ polycyclic hydrocarbyl group comprising a hydroxyl group, a lactone group, or a combination thereof, or —[(CH$_2$)$_n$—Y—SO$_3^-$Z$^+$], wherein n is 0, 1, or 2; Y is a $C_{1-4}$ alkylene group comprising at least one fluorine atom, provided that when n is 0, Y is a $C_{2-4}$ alkylene group comprising at least one fluorine atom; and $Z^+$ is an organic cation;
$R^3$ and $R^4$ are each independently hydrogen, cyano, $C_{1-6}$ alkyl, $C_{1-6}$ fluoroalkyl, optionally substituted $C_{6-12}$ aryl, or —C(O)O—$R^{11}$ wherein $R^{11}$ is a $C_{1-20}$ alkyl group optionally comprising one or more heteroatoms; and
Q is

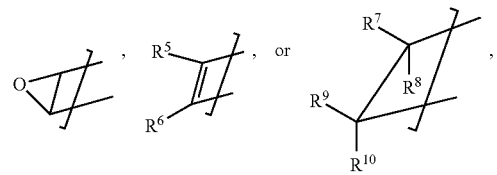

wherein
$R^5$ and $R^6$ are each independently hydrogen, fluorine, cyano, trifluoromethyl, $C_{1-6}$ alkyl, $C_{6-20}$ hydrocarbyl comprising a lactone group, or —O$R^{12}$ wherein $R^{12}$ is $C_{1-20}$ alkyl, or $C_{6-20}$ hydrocarbyl comprising a lactone group; and
$R^7$, $R^8$, $R^9$, and $R^{10}$ are each independently hydrogen; hydroxyl; —O$R^{13}$ wherein $R^{13}$ is a $C_{1-20}$ hydrocarbyl group optionally comprising one or more heteroatoms; —S$R^{13}$ wherein $R^{13}$ is defined above; —OC(O)$R^{13}$ wherein $R^{13}$ is defined above; —N($R^{14}$)C(O)$R^{13}$ wherein $R^{13}$ is defined above and $R^{14}$ is hydrogen or a $C_{1-20}$ hydrocarbyl group optionally comprising one or more heteroatoms; —[OC(O)—C($R^a$)=CH$_2$] wherein $R^a$ is hydrogen or fluoro or cyano or $C_{1-10}$ alkyl or $C_{1-10}$ fluoroalkyl; —[S—(CH$_2$)$_n$—Y—SO$_3^-$Z$^+$] wherein n, Y, and $Z^+$ are defined above, —[S—(CH$_2$)$_n$—Y—SO$_3^-$Z$^+$] wherein n, Y, and $Z^+$ are defined above, or —[O—C(O)—(CH$_2$)$_n$—Y—SO$_3^-$Z$^+$] wherein n, Y, and $Z^+$ are defined above; and
X is —CH$_2$—, —O—, —C(O)—, —S(O)—, or —S(O)$_2$—;
provided that the photoacid-generating compound comprises
exactly one occurrence of —[(CH$_2$)$_n$—Y—SO$_3^-$Z$^+$],
1 or 2 occurrences of the $C_{6-20}$ polycyclic hydrocarbyl group comprising a hydroxyl group, a lactone group, or a combination thereof, and
1, 2, or 3 total occurrences of hydroxyl groups and lactone groups; and provided that when Q is

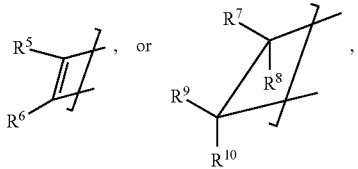

and $R^5$, $R^6$, $R^7$, $R^8$, $R^9$, and $R^{10}$ are hydrogen, and $R^2$ is —[(CH$_2$)$_n$—Y—SO$_3^-$Z$^+$], then
$R^1$ excludes —C(O)O— groups and —S(O)$_2$— groups.

2. The photoacid-generating compound of claim 1, wherein Q is

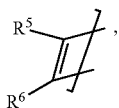

wherein $R^5$ and $R^6$ are hydrogen; and $R^2$ is

—[(CH$_2$)$_n$—Y—SO$_3^-$Z$^+$], wherein n is 0, 1, or 2; Y is a C$_{1-4}$ alkylene group comprising at least one fluorine atom, provided that when n is 0, Y is a C$_{2-4}$ alkylene group comprising at least one fluorine atom; and Z$^+$ is an organic cation.

3. The photoacid-generating compound of claim 1, wherein Q is

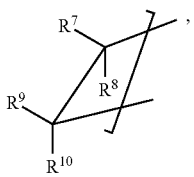

wherein one of $R^7$ and $R^8$ is hydroxyl and the other of $R^7$ and $R^8$ is hydrogen; wherein one of $R^9$ and $R^{10}$ is [O—(CH$_2$)$_n$—Y—SO$_3^-$Z$^+$], —[OC(O)—(CH$_2$)$_n$—Y—SO$_3^-$Z$^+$], or —[S—(CH$_2$)$_n$—Y—SO$_3^-$Z$^+$], and the other of $R^9$ and $R^{10}$ is hydrogen; and $R^2$ is a C$_{8-12}$ polycyclic hydrocarbyl group comprising a hydroxyl group, a lactone group, or a combination thereof.

4. The photoacid-generating compound of claim 1, wherein Q is

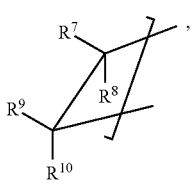

wherein $R^7$ and $R^9$ are hydrogen; wherein one of $R^8$ and $R^{10}$ is [O—(CH$_2$)$_n$—Y—SO$_3^-$Z$^+$] or —[S—(CH$_2$)$_n$—Y—SO$_3^-$Z$^+$] or —[O—C(O)—(CH$_2$)$_n$—Y—SO$_3^-$Z$^+$] wherein n is 0, 1, or 2, Y is a C$_{1-4}$ alkylene group comprising at least one fluorine atom, and Z$^+$ is an organic cation, and the other of $R^8$ and $R^{10}$ is hydrogen; and $R^2$ is a C$_{8-12}$ polycyclic hydrocarbyl group comprising a hydroxyl group, a lactone group, or a combination thereof.

5. The photoacid-generating compound of claim 1, wherein Q is

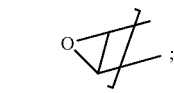

and
$R^2$ is

—[(CH$_2$)$_n$—Y—SO$_3^-$Z$^+$], wherein n is 0, 1, or 2; Y is a C$_{1-4}$ alkylene group comprising at least one fluorine atom, provided that when n is 0, Y is a C$_{2-4}$ alkylene group comprising at least one fluorine atom; and Z$^+$ is an organic cation.

6. The photoacid-generating compound of claim 1, selected from the group consisting of

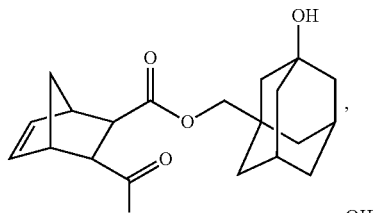

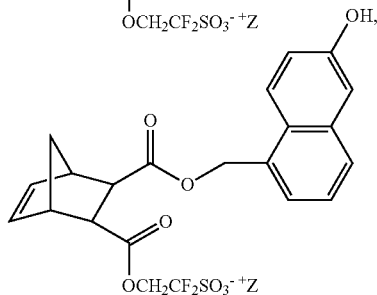

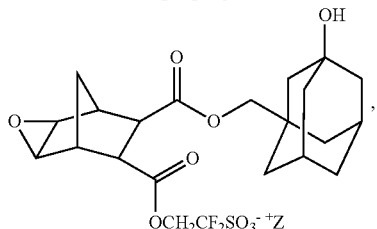

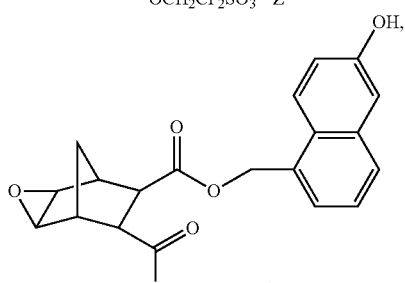

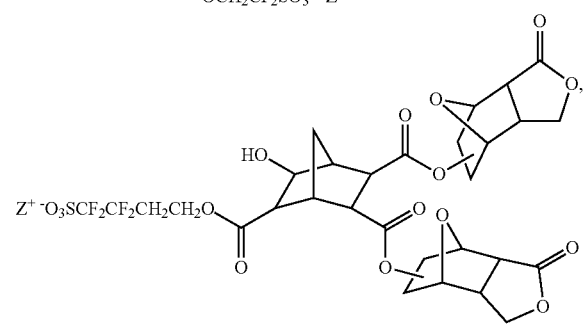

-continued

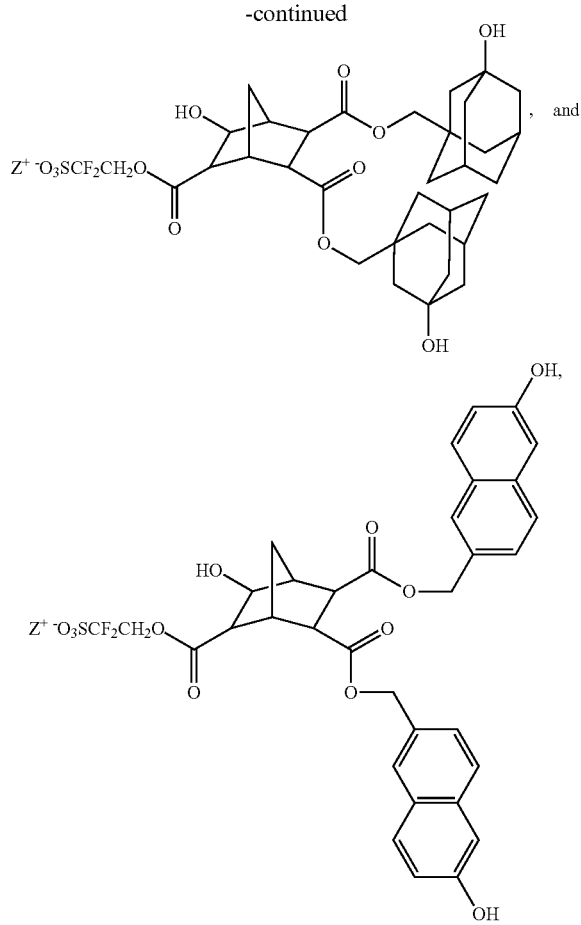

wherein Z⁺ is an organic cation.

7. The photoacid-generating compound of claim 1, wherein Q is

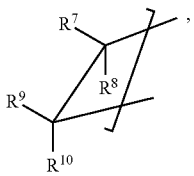

wherein one of $R^7$ and $R^9$ is hydrogen or hydroxyl and the other of $R^7$ and $R^9$ is hydrogen; wherein one of $R^8$ and $R^{10}$ is —[OC(O)C($R^a$)=CH$_2$] wherein $R^a$ is hydrogen, fluoro, cyano, $C_{1-10}$ alkyl, or $C_{1-10}$ fluoroalkyl, and the other of $R^8$ and $R^{10}$ is hydrogen; and wherein $R^2$ is —[(CH$_2$)$_n$—Y—SO$_3^-$Z⁺], wherein n is 0, 1, or 2; Y is a $C_{1-4}$ alkylene group comprising at least one fluorine atom, provided that when n is 0, Y is a $C_{2-4}$ alkylene group comprising at least one fluorine atom; and Z⁺ is an organic cation.

8. A polymer comprising repeat units derived from the photoacid-generating compound of claim 7.

9. A photoresist composition comprising the photoacid-generating compound of claim 1.

10. A method of forming a photoresist relief image, comprising:
(a) applying a layer of the photoresist composition of claim 9 on a substrate to form a photoresist layer;
(b) pattern-wise exposing the photoresist layer to activating radiation to form an exposed photoresist layer; and
(c) developing the exposed photoresist layer to provide a photoresist relief image.

11. A photoresist composition comprising the polymer of claim 8.

* * * * *